(12) United States Patent
Levasseur et al.

(10) Patent No.: US 10,543,010 B2
(45) Date of Patent: Jan. 28, 2020

(54) MEDICAL DEVICE AND RELATED METHODS

(71) Applicant: Boston Scientific Scimed, Inc., Maple Grove, MN (US)

(72) Inventors: Amy Levasseur, Holliston, MA (US); Kirsten Viering, Watertown, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 457 days.

(21) Appl. No.: 15/215,999

(22) Filed: Jul. 21, 2016

(65) Prior Publication Data

US 2017/0020548 A1 Jan. 26, 2017

Related U.S. Application Data

(60) Provisional application No. 62/196,111, filed on Jul. 23, 2015.

(51) Int. Cl.
*A61B 17/32* (2006.01)
*A61B 17/00* (2006.01)

(52) U.S. Cl.
CPC ........... *A61B 17/320016* (2013.01); *A61B 2017/00818* (2013.01); *A61B 2017/32004* (2013.01)

(58) Field of Classification Search
CPC . A61B 1/00098; A61B 1/018; A61B 1/00154; A61B 1/00082; A61B 1/00087; A61B 1/0125; A61B 1/32; A61B 1/00089; A61B 1/00135; A61B 2017/0225; A61B 17/0218; A61B 17/3423; A61B 18/1492; A61B 2018/00601; A61M 25/09; A61F 2002/041; A61F 2/04
See application file for complete search history.

(56) References Cited

U.S. PATENT DOCUMENTS

| 6,458,074 | B1* | 10/2002 | Matsui | ............... A61B 1/00098 600/104 |
| 8,475,360 | B2 | 7/2013 | Brown | |
| 2005/0107664 | A1 | 5/2005 | Kalloo et al. | |

(Continued)

FOREIGN PATENT DOCUMENTS

| DE | 19962209 A1 | 6/2000 |
| EP | 2228002 A1 | 9/2010 |

(Continued)

OTHER PUBLICATIONS

International Search Report and Written Opinion issued in PCT/US2016/043449, dated Oct. 14, 2016 (11 pages).

*Primary Examiner* — Ryan J. Severson
*Assistant Examiner* — Mohamed G Gabr
(74) *Attorney, Agent, or Firm* — Bookoff McAndrews, PLLC

(57) ABSTRACT

The present disclosure is directed to a medical device. Systems and methods are provided for accessing and visualizing the pancreatico-biliary system. The medical device may include a guide catheter with a first lumen and a second lumen. A first elevator may be disposed in the first lumen, wherein the first elevator is movable relative to the first lumen for elevating a first tool insertable into the first lumen. A second elevator may be disposed in the second lumen, wherein the second elevator is movable relative to the second lumen for elevating a second tool insertable into the second lumen.

17 Claims, 6 Drawing Sheets

(56) References Cited

U.S. PATENT DOCUMENTS

| | | | |
|---|---|---|---|
| 2007/0265494 A1 | 11/2007 | Leanna et al. | |
| 2013/0144118 A1* | 6/2013 | Piskun | A61B 1/00082 600/104 |
| 2014/0336464 A1 | 11/2014 | Firstenberg | |
| 2015/0073391 A1 | 3/2015 | Hutchins et al. | |

FOREIGN PATENT DOCUMENTS

| | | |
|---|---|---|
| JP | 2001037710 A | 2/2001 |
| WO | WO 2011/084616 A2 | 7/2011 |
| WO | WO 2013/140172 A1 | 9/2013 |

* cited by examiner

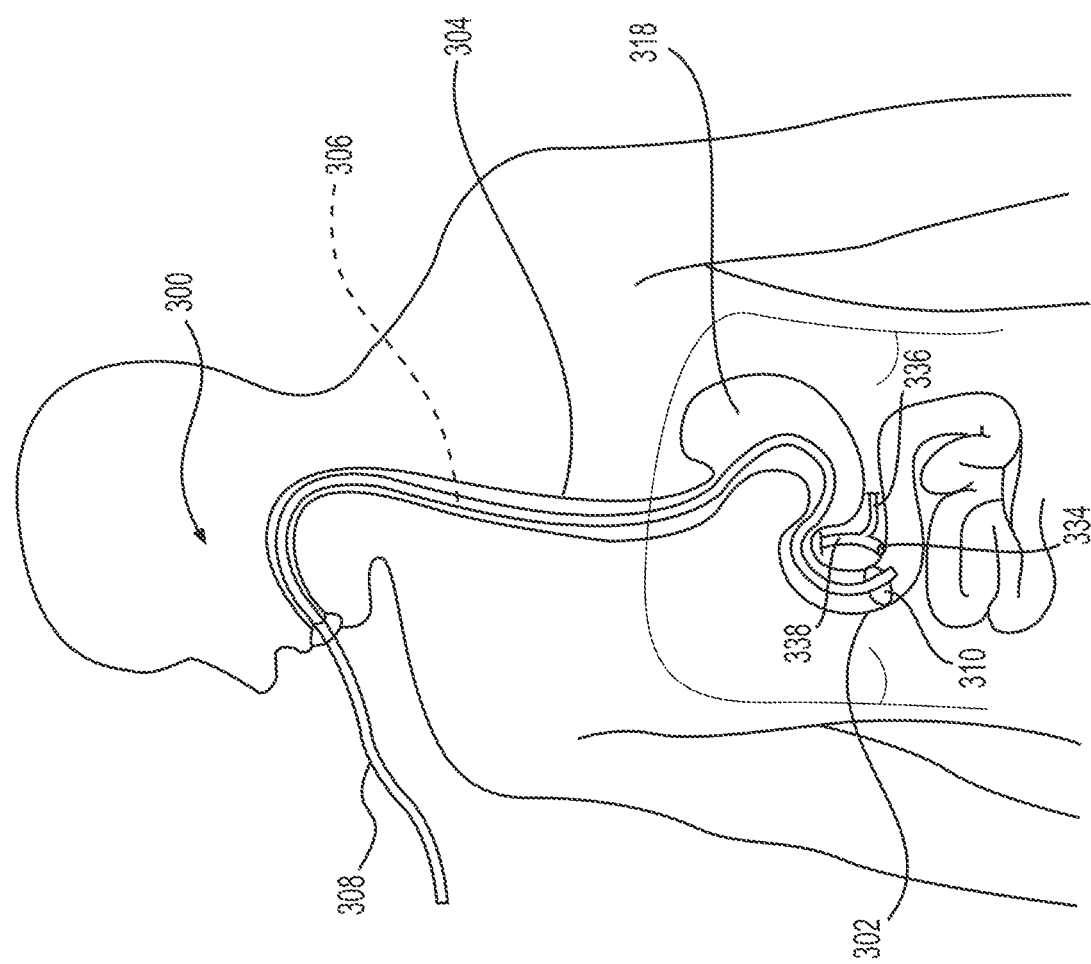

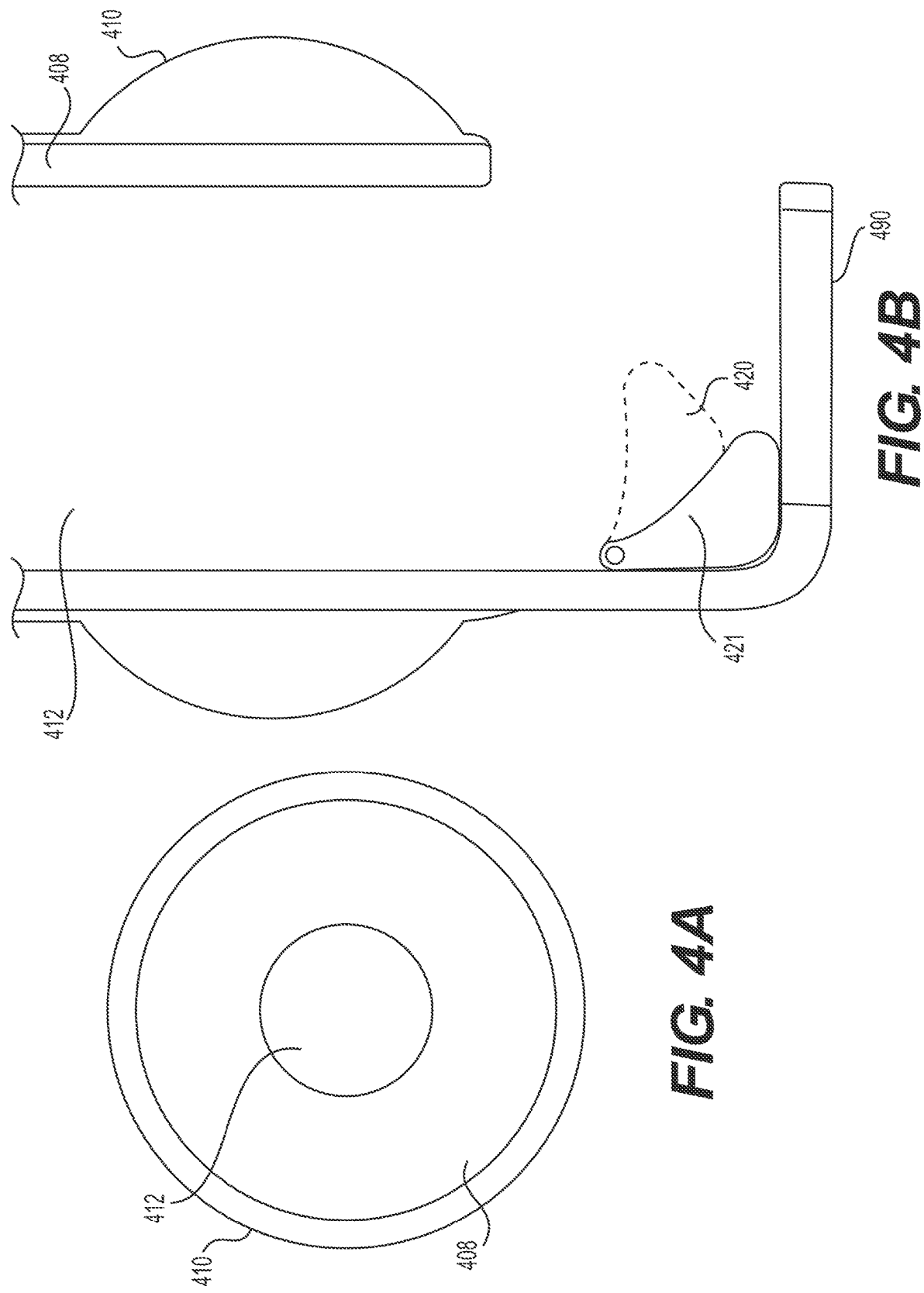

MEDICAL DEVICE AND RELATED METHODS

CROSS-REFERENCE TO RELATED APPLICATIONS

This application claims the benefits of priority from U.S. Provisional Application No. 62/196,111, filed on Jul. 23, 2015, the entirety of which is incorporated herein by reference.

DESCRIPTION OF THE EMBODIMENTS

Technical Field

Embodiments of the present disclosure relate generally to medical instruments. More particularly, embodiments of the disclosure relate to medical instruments for use in medical applications, such as, for example, obtaining visualization of the pancreatico-biliary system. Embodiments of the disclosure also cover methods of using such instruments.

Background of the Disclosure

Various diagnostic and/or therapeutic procedures require visualization of the pancreatico-biliary system, including the hepatics ducts. In order to gain access to the pancreatico-biliary system, conventional solutions use a re-usable endoscope, such as, e.g., a duodenoscope. In most cases, a tome is used in conjunction with the duodenoscope to gain access. Once access is achieved, the endoscope, e.g., duodenoscope, may be used as a delivery system for delivering a visualization device to the pancreatico-biliary system.

Such conventional solutions, however, include a re-useable duodenoscope that must be thoroughly cleaned between procedures. Cleaning a duodenoscope requires both time and money. In addition, due to its many small and long channels, as well as a large number of parts within the endoscope, it may be difficult to completely clean the duodenoscope. In fact, the re-usable duodenoscope has been associated with problems relating to cleaning, leading to documented cases of infection of multiple patients. Therefore, there exists a need for a single-use medical device for delivering visualization devices to the pancreatico-biliary system.

Further, conventional endoscopes generally include a single elevator, which limits the ability to direct multiple devices (from a single or multiple lumens) to a target location. Further, the single elevator does not allow two devices within separate lumens to both be directed at different angles. Thus, there exists a need for additional options for sufficiently directing tools, devices, etc. to targeted treatment sites

SUMMARY OF THE DISCLOSURE

Embodiments of the present disclosure provide systems and methods for performing various medical procedures, including obtaining visualization of the pancreatico-biliary system.

One example of the present disclosure is directed to a medical device. The medical device may include a guide catheter with a first lumen and a second lumen. A first elevator may be disposed in the first lumen, wherein the first elevator is movable relative to the first lumen for elevating a first tool insertable into the first lumen. A second elevator may be disposed in the second lumen, wherein the second elevator is movable relative to the second lumen for elevating a second tool insertable into the second lumen.

Examples of the medical device may additionally and/or alternatively include one or more other features. For example, the first and second elevators may be rotatable about a pivot axis that rotatably couples the at least one of the first and second elevators to the guide catheter. In another example, the first elevator may be rotatable independent of the second elevator. The first elevator may be rotatable in unison with the second elevator. The medical device may include at least one of the first tool and the second tool, wherein the at least one of the first tool and the second tool includes at least one of an imaging device and an access device. The access device may be one of a needle-knife and a tome. The imaging device and the access device may be disposed within the first lumen and the second lumen, respectively. One of the imaging device and the access device may be disposed in the first lumen and the other is disposed with the second lumen. The imaging device may be disposed in the first lumen. The first lumen may have a first diameter and the second lumen may have a second diameter smaller than the first diameter. The medical device may include an expandable portion disposed on the outside of the guide catheter. The medical device may include an expanding apparatus, configured to expand the expandable portion. The medical device may include a first elevator control mechanism at a proximal end of the medical device that is configured to rotate the first elevator, and a second elevator control mechanism at the proximal and of the medical device that is configured to rotate the second elevator. The first elevator control mechanism and the second elevator control mechanism may be located on a handle portion. The medical device may include a sheath surrounding the guide catheter and fluidly connected to the expandable portion.

One example of the present disclosure is directed to a guide catheter assembly. The guide catheter assembly may include a shaft, a first lumen extending through the shaft, and a first elevator in the first lumen, wherein the first elevator is movable relative to the first lumen. The guide catheter assembly may also include a second lumen extending through the shaft, a second elevator in the second lumen, wherein the second elevator is movable relative to the second lumen. An expandable portion may be disposed around at least a portion of the guide catheter assembly.

Examples of the guide catheter assembly may additionally and/or alternatively include one or more other features. For example, the first elevator may be rotatable independently of the second elevator. The first elevator and the second elevator may be rotatable in unison. The guide catheter assembly may include an exterior and a sheath at least partially sealed to the exterior and fluidly connected to the expandable portion. The guide catheter assembly may further comprise a first tool insertable within the first lumen and a second tool insertable within the second lumen. The first tool may be at least one of a needle-knife, tome, and imaging device.

One exemplary embodiment of the present disclosure may be directed to a method for positioning a first tool and a second tool using a guide catheter. The method may include inserting the guide catheter into a patient, wherein the guide catheter includes a distal end portion having a first elevator for engaging the first tool and a second elevator for engaging the second tool. The method may also include adjusting a position of the first elevator to adjust a position of the first tool relative to the distal end portion of the guide catheter, and adjusting a position of the second elevator to adjust a position of the second tool relative to the distal end portion of the guide catheter.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the scope of disclosed embodiments, as set forth by the claims.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 3A illustrates an exemplary embodiment of a guide catheter of a delivery system inserted into a patient's natural body orifice;

FIG. 4A illustrates an exemplary alternative embodiment of a cross-section of the guide catheter;

FIG. 4B illustrates an exemplary alternative embodiment of a distal portion of the guide catheter;

DESCRIPTION OF THE EMBODIMENTS

Reference will now be made in detail to exemplary embodiments of the disclosure, examples of which are illustrated in the accompanying drawings. Wherever possible, the same reference numbers will be used throughout the drawings to refer to the same or like parts. The term "distal" refers to a position farther away from an operator end of the device. The term "proximal" refers a position closer to the operator end of the device. As used herein, the term "approximately" indicates a range of values within +/−5% of a stated value.

Embodiments of the present disclosure relate to systems for performing various medical procedures and methods for obtaining visualization of the pancreatico-biliary system and/or any other suitable patient anatomy. The medical device embodiments described herein is a single-use delivery system. More specifically, in exemplary embodiments, the medical device is configured to deliver and position a visualization device and/or an access device, e.g., a needle-knife and/or a tome, for accessing the papilla of Vater or major papilla. The papilla of Vater generally forms the opening where the pancreatic duct and the common bile duct empty into the duodenum of the small intestine. The hepatic ducts and the gall bladder empty into the common bile duct. In general, an endoscopic or biliary procedure may require advancing a medical device to a suitable location along the biliary tree and then performing the appropriate intervention. The medical device and methods disclosed herein provide access and visualization (and a delivery system for visualization and access devices) to, among other areas, the papilla and/or pancreatico-biliary system.

Figure 1:
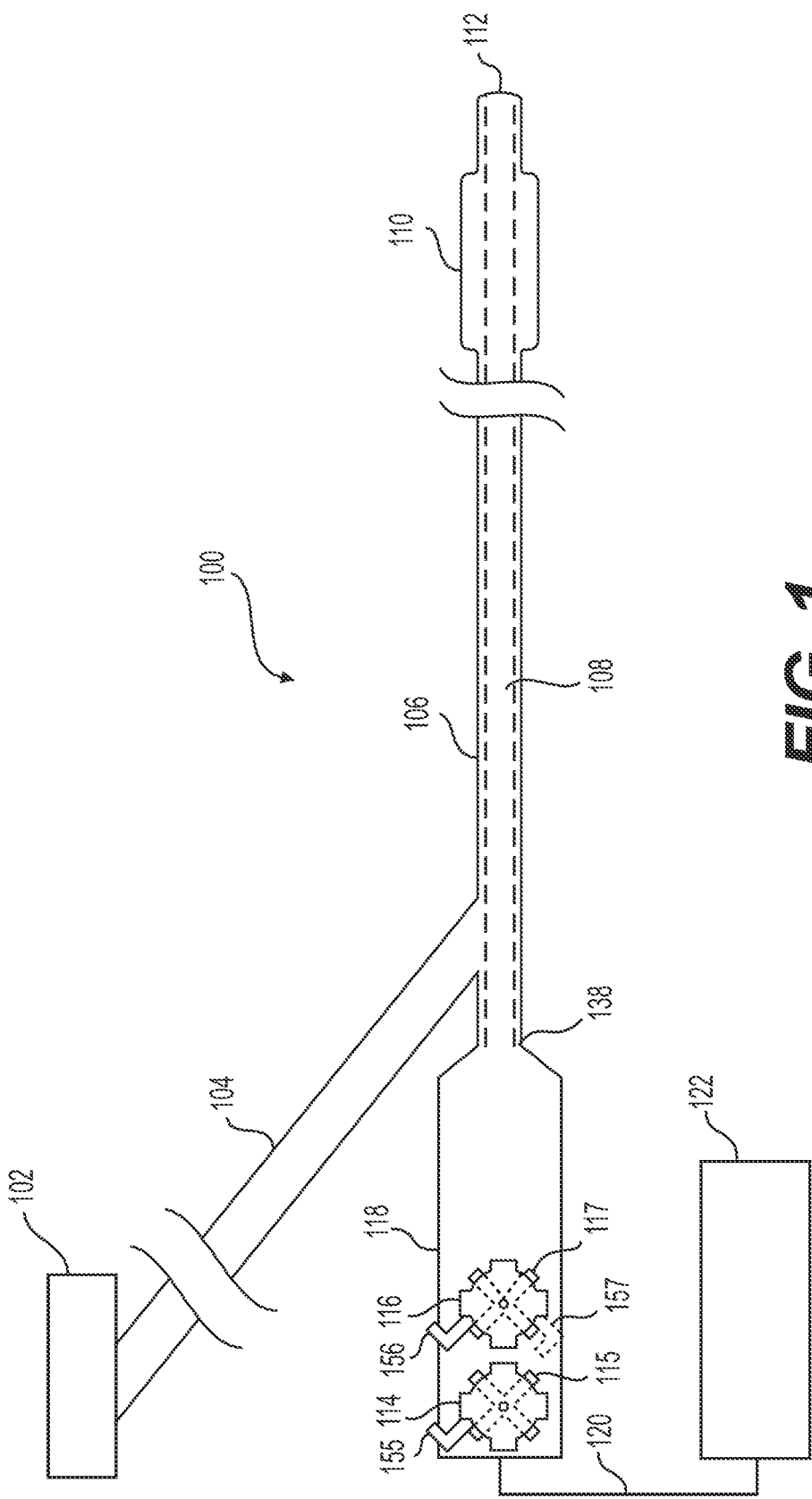
FIG. 1 illustrates an exemplary embodiment of a medical device.

FIG. 1 illustrates an exemplary embodiment of a medical device 100. Medical device 100 may include a guide catheter 108, a handle portion 118, controller 122, expanding apparatus 102, and/or expandable portion 110.

Guide catheter 108 may have any suitable cross-sectional shape and/or configuration and may be any desired dimension that can be received in the desired bodily orifice and corresponding tract. Guide catheter 108 may be configured for insertion into a patient's body through an anatomical opening. Accordingly, guide catheter 108 may be shaped and sized for placement into a patient via a natural body orifice or an incision.

The guide catheter 108 extends between the proximal end 138 and the distal end 112. The guide catheter 108 may have any suitable length. The length of guide catheter 108 may vary depending upon patient need. For example, the length of the guide catheter 108 may be sufficient so that the proximal end 138 is external to the patient's body and the distal end 112 is internal to the patient's body. In certain embodiments, the distal end 112 extends through an anatomical opening (i.e. the patient's mouth or nose) and may be disposed within the small intestine.

The diameter of guide catheter 108 may be selected based on the desired application, with the largest diameter of guide catheter 108 generally chosen to be smaller than the typical stretched or unstretched diameter of the desired body lumen where guide catheter 108 may be used. A guide catheter to be employed in the esophagus, for example, may be smaller than a guide catheter to be employed in the colon. In some examples, guide catheter 108 may be approximately 5 mm to approximately 15 mm, or approximately 11 mm.

In one embodiment, guide catheter 108 may be a tubular structure. This structure may have a substantially circular cross-section or an elliptical, oval, polygonal, or irregular cross-section may be employed, as desired. In addition, a select portion of guide catheter 108, such as, e.g., a distal portion, may have a cross-sectional configuration or dimension different from another portion, e.g., a proximal portion, of guide catheter 108.

Guide catheter 108 may be flexible along its entire length or adapted for flexure along portions of its length. Alternatively, the distal end of guide catheter 108 may be flexible while the remainder of guide catheter 108 may be semi-rigid or otherwise relatively less flexible. Flexibility allows guide catheter 108 to maneuver turns in body lumens, while some level of rigidity provides a structure upon which the operator can exert the necessary force to urge guide catheter 108 as necessary.

Guide catheter 108 may be a tube made from any suitable biocompatible material known to one of ordinary skilled in the art having sufficient flexibility to traverse a digestive tract. Such materials may include, but are not limited to, rubber, silicone, silicone rubber, synthetic plastics, and/or polymers, such as a polyolefin triblock polymer like poly (Styrene-block-IsoButylene-block-styrene)(SIBS), latex, polyurethane, polytetrafluoroethylene (PTFE), ethylene tetrafluoroethylene (ETFE), perfluoroalkoxy (PFA), polyether ether ketone (PEEK), high density polyethylene (HDPE), and/or polypropylene (PP). In another example, the material forming guide catheter 108 may be a superelastic material such as nitinol, which is a nickel-titanium alloy. In yet another example, guide catheter 108 may include one or more metals and/or alloys. Guide catheter 108 may be coated using suitable low friction material, such as TEFLON®, polyetheretherketone (PEEK), polyimide, nylon, polyethylene, or other lubricious polymer coatings, to reduce surface friction with the surrounding body tissues.

Handle portion 118 may be disposed at and attached to proximal end 138 of guide catheter 108. Handle portion 118 may be any known, suitable handle. Handle portion 118 may be externally manipulated by the user to facilitate entry and removal of guide catheter 108, operate expanding apparatus 102, and/or operate mechanisms disposed at or near the distal end 112 of guide catheter 108. Further, in an alternative embodiment, the operation of the medical device and, in particular, the mechanisms disposed at the distal end 112 may be operated wirelessly.

As shown in the example illustrated in FIG. 1, handle 118 may include control mechanisms 114, 115, 116, and/or 117. As shown in FIG. 1, control mechanisms 114 and 115 may be stacked, e.g., control mechanism 114 may be positioned radially outward of control mechanism 115 relative to handle 118. Similarly, control mechanisms 116 and 117 may be stacked. In some examples, control mechanisms may be steering mechanisms and/or elevator control mechanisms. In some examples, the radially outward/"top" control mechanisms, e.g., control mechanisms 114 and 116 may be steering mechanisms and the radially inward/"bottom" control mechanism, e.g., control mechanisms 115 and 117 may be elevator control mechanisms, (or vice versa). In some examples, the distal control mechanisms, e.g., control mechanisms 116 and 117, may be steering mechanisms and the proximal control mechanisms, e.g., control mechanisms 114 and 115, may be elevator mechanisms, (or vice versa).

Elevator control mechanisms 114 and 116 may be rotatable knobs. Alternatively, elevator control mechanisms 114 and 116 may include pivotable levers, similar to levers 155 and 156. Elevator control mechanisms 114 and 116 may control the movements of a first elevator and/or a second elevator located at or near the distal end 112 of guide catheter 108. In some examples, the elevator(s) and/or associated elevator control mechanisms may position an imaging device and/or access device in relation to a target location. The target location may be, for example, a location in which tools disposed within guide catheter 108 are capable of accessing the target papilla, e.g., the Papilla of Vater or major papilla. FIG. 1 is merely exemplary, however. Medical device 100 may include any number of elevator control mechanisms. In some examples, such as those with a single elevator or in which multiple elevators operate in unison, medical device 100 may include a single elevator control mechanism. In some embodiments, the handle 118 may not include any elevator control mechanisms at all. Elevators within medical device 100 may be controlled by any suitable mechanisms, e.g., levers, pull wires, gears, computerized mechanisms, rods, rotatable knobs (as shown in FIG. 1), etc. In some embodiments, the elevators are fixed in position, rather than rotatable. In addition, handle 118 may include any number of other controls, mechanisms, and/or devices.

Medical device 100 and/or handle 118 may additionally or alternatively include locking mechanisms for locking a first elevator and/or a second elevator located at or near the distal end 112 of guide catheter 108. In one example, the locking mechanisms of handle 118 may be elevator lock levers, e.g., levers 155 and 156. Lever 157 illustrates a position of lever 156 that locks the associated elevator in its current position. Medical device 100 may include any number of locking mechanisms. In some examples, such as those with a single elevator or in which multiple elevators operate in unison, medical device 100 may include a single locking mechanism, e.g., lever 155 or 156. In some embodiments, medical device 100 and/or handle 118 may not include any locking mechanisms. Levers 155 and 156 may lock the elevators by locking or otherwise restricting rotation or pivoting of elevator control mechanisms 114 and 116. The locking/restriction may be achieved by increasing friction between components to prevent relative movement between the components, thereby restricting movement of elevator control mechanisms 114 and 116.

Steering mechanisms 115 and 117 may steer guide catheter 108. In one example, guide catheter 108 may be flexible, adapted for flexible steering within bodily lumens, as understood in the art. Steering mechanisms 115 and 117 may move at least a portion of guide catheter 108 (e.g., distal end 112) up/down and/or side-to-side. Additional degrees of freedom, provided for example via rotation, translational movement of guide catheter 108, or additional articulation of bending sections, may also be implemented. Steering mechanisms 115 and 117 may be rotatable knobs. Knob controlled steering may allow two-way deflection of guide catheter 108. In addition to, or as an alternative to, steering mechanisms 115 and 117 and/or rotational knobs, guide catheter 108 may include any suitable steering system, including at least one of or all of pulleys, control wires, gearing, and electrical actuators.

Expandable portion 110 may be, for example, incorporated in guide catheter 108 and/or fixed along the outside of guide catheter 108. In some embodiments, guide catheter 108 may be disposed within a sheath 106. In some examples, expandable portion 110 may be included in and/or integral with a distal portion of sheath 106. Expandable portion 110 may be positioned a suitable distance, e.g., approximately 1.0 cm to approximately 4 cm or approximately 2.5 cm, proximally of the distal end 112 of guide catheter 108. A suitable distance may provide sufficient stability for delivery of the visualization device and/or access device, while providing sufficient flexibility to accurately position the distal end 112 of guide catheter 108. In some embodiments, expandable portion 110 may be a balloon. In some embodiments, the expandable portion 110 may be at a fixed position relative to the guide catheter 108. In some embodiments, expandable portion 110 may be movable relative to the longitudinal axis of guide catheter 108.

Sheath 106 may be fluidly connected to expanding apparatus 102 via a lumen 104. Expanding apparatus 102 may be any device capable of introducing fluid to lumen 104, including but not limited to, a pump, a syringe, and/or a pressurized tank. Expanding apparatus 102 may be used to introduce fluid into lumen 104, through sheath 106, and into expandable portion 110. The introduction of fluid into expandable portion 110 may increase the pressure on the walls of expandable portion 110 and cause the expandable portion 110 to inflate or otherwise expand. In some embodiments, the expanding apparatus 102 and/or the expandable portion 110 may be configured to expand expandable portion 110 to a variety of different diameters. The expandable portion 110 may be configured to expand to a range of any desired diameter or to several distinct diameters (e.g., three diameters) at the same number (e.g., three) separate pressures. Expandable portion 110 may expand to a diameter of between approximately 5 mm to approximately 25 mm or approximately 10 mm to approximately 20 mm. In some embodiments, the expandable portion 110 may include tapered shoulders or rounded shoulders.

Sheath 106, expanding apparatus 102, and/or lumen 104 are merely exemplary. Expandable portion 110 may be expanded in any way, including but not limited to, a lumen within the guide catheter 108 supplying fluid to expandable portion 110. FIG. 1 illustrates sheath 106 extending from handle 118 to the distal end 112 of guide catheter 108. The span of sheath 106 is not limited thereto, however. Sheath 106 may be any length that allows lumen 104 and expandable portion 110 to be fluidly connected. For example, sheath 106 may terminate at any point proximal to lumen 104 and distal to expandable portion 110. The proximal and distal ends of sheath 106 may be sealed to guide catheter 108, e.g., to ensure that the expanding fluid does not enter the patient's body and/or to provide sufficient pressure to expand the expanding portion 110 to the desired diameter.

In one example, medical device 100 may attach to or include a controller 122. Controller 122 may be connected to handle 118 of medical device 100 via wires 120. Controller 122 may control and/or allow an operator to control the operation of various components of medical device 100. For example, controller 122 may connect to and/or control a visualization device (e.g., SpyScope™) slidably disposed within a lumen of guide catheter 108. In one example, controller 122 may control the movement of elevator(s) at or near the distal end 112 of guide catheter 108. Controller 122 may receive and/or process electrical signals received from medical device 100, including imaging signals from any imaging device within a lumen of guide catheter 108 and/or associated with guide catheter 108. Controller 122 also may perform a variety of tasks depending on the nature of medical device 100, such as determining the geometry characteristics of a region of interest, activating and deactivating the expanding apparatus 102 to expand (e.g., inflate) and/or constrict (e.g., deflate) expandable portion 110, and/or generating images of the region of interest for output to a display (not shown). In some implementations, medical device 100 may include and/or controller 122 may control other components, including, but not limited to, a vacuum source, a coolant source, and/or a laser source.

Figure 2:
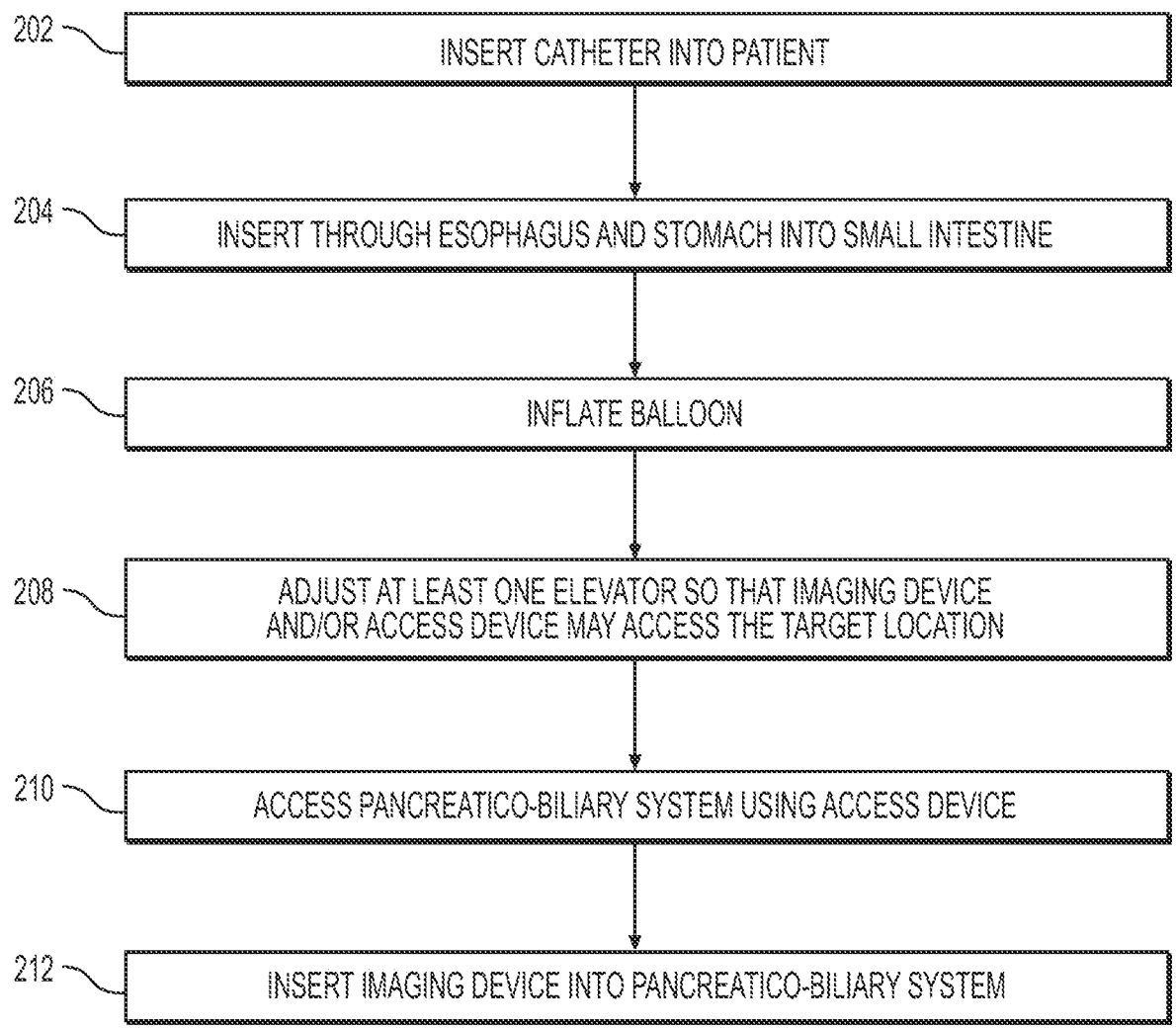
FIG. 2 is a block diagram of an exemplary method of using embodiments of the medical device disclosed herein.

Controller 122 may perform, in whole or in part, exemplary methods described in further detail with respect to method 200 of FIG. 2. In some implementations, controller 122 may include, for example and without limitation, a processor, and memory for executing and storing processor-readable instructions. The memory may include any type of random access memory (RAM) or read-only memory (ROM) embodied in a physical storage medium, such as magnetic storage including floppy disk, hard disk, or magnetic tape; semiconductor storage such as solid state disk (SSD) or flash memory; optical disc storage; cloud storage; Digital Imaging and Communications in Medicine (DICOM) compatible storage; or magneto-optical disc storage. Software may include one or more applications and an operating system.

FIG. 2 is a process flow diagram of an exemplary method 200 for accessing/visualizing the pancreatico-biliary system within the patient. For purposes of discussion, method 200 will be described using medical device 100 of FIG. 1 and guide catheter 308 and patient 300 of FIGS. 3A and 3B, but method 200 is not intended to be limited thereto. As shown in FIG. 2, method 200 includes steps 202, 204, 206, 208, 210, and 212. However, it should be noted that method 200 may include more or fewer steps as desired for a particular implementation and the steps may be performed in any order. In an example, one or more of the above-listed steps of method 200 may be executed by an operator, medical device 100, and/or controller 122 of FIG. 1, as described above. However, method 200 is not intended to be limited thereto, and the steps of method 200 may be performed by any party, module, device, and/or server.

Method 200 may begin at step 202, which may include inserting a catheter into a patient. For example, FIG. 3A illustrates an exemplary schematic view of step 202, inserting guide catheter 308 into patient 300. It is contemplated that medical device 100 may be used as guide catheter 308. While this disclosure relates to the use of the disclosed system in the digestive tract of a human subject, it is understood that the features of this disclosure could be used in other locations (other organs and tissue) within a patient. In step 202, at least a portion of the catheter of the medical device may be inserted into the nose or mouth (or other suitable natural body orifices) of a patient's body. In step 204, the catheter may be further inserted through the esophagus, stomach, and into the small intestine until it reaches the target location. For example, an operator may insert and extract the guide catheter 308 through the gastrointestinal tract including, but not limited to, the esophagus 306, stomach 318, and the small intestine 302. The length of the guide catheter 308 may be sufficient so that the proximal end of guide catheter 308 is external to the patient's body and the distal end of guide catheter 308 is internal to the patient's body, e.g. within the small intestine 302.

Figure 3B:
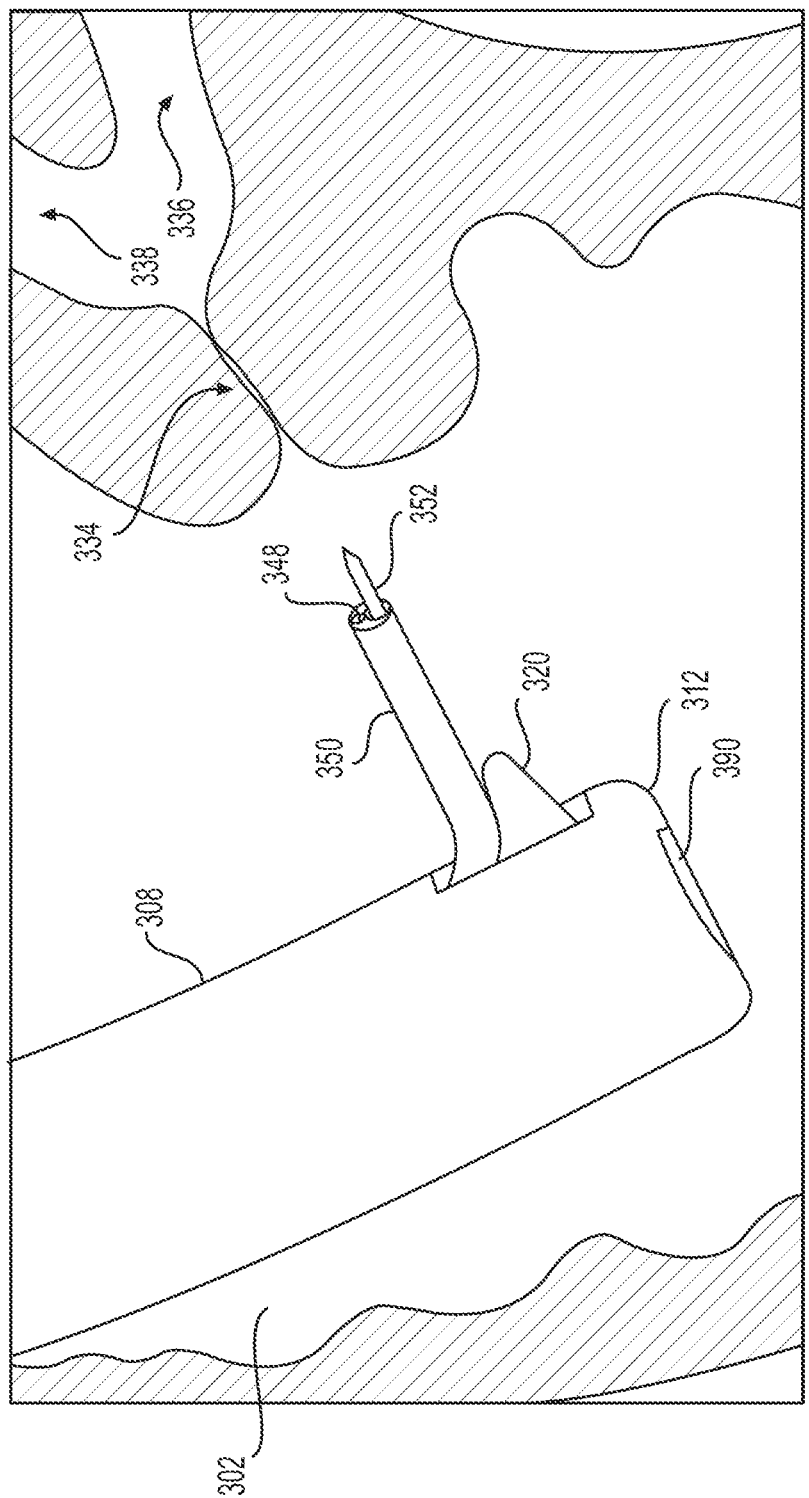
FIG. 3B illustrates an exemplary embodiment of the guide catheter (and various tools disposed therein) in a position to access the pancreatico-biliary system of the patient.

The guide catheter 308 may extend into the patient's body until it reaches a position in which tools disposed within the guide catheter 308 can access the target location. In examples in which the medical device is being used to access and visualize aspects of the pancreatico-biliary system, this position may be, for example, the duodenum of the small intestine 302. In such examples, the target location may be the papilla of Vater 334 located in a portion of the duodenum of the small intestine 302. FIG. 3B illustrates an overview of a biliary system or tree of patient 300. For the purpose of this disclosure, the papilla of Vater 334 is understood to be of the same anatomical structure as the ampulla of Vater. The papilla of Vater 334 generally forms the opening where the pancreatic duct 336 and the common bile duct 338 empty into the duodenum of the small intestine 302. The hepatic ducts and the gall bladder empty into the common bile duct 338 (also referred to as the bile duct). In some embodiments, accessing a target location within the biliary tree may require advancing the guide catheter 308 through the duodenum of the small intestine 302 to a position adjacent to the papilla of Vater 334. In some examples, being in a position in which tools disposed within the guide catheter may reach the target location may require rotating the guide catheter. For example, as illustrated in FIG. 3B, it may be desired that the tools reach papilla 334, located to the right of guide catheter 308 as positioned in FIG. 3B. Guide catheter 308 may need to be rotated until an opening in which tools may exit guide catheter 308 is facing papilla 334, e.g., facing the right of FIG. 3B. In some examples, an imaging device (a camera and/or a SpyScope™ device manufactured and sold by Boston Scientific Corporation) may be disposed within the catheter during insertion and positioning. For example, the imaging device may be used to find the target location. In one example, the imaging device may be pointed toward the distal end 312 of guide catheter 308. Guide catheter 308 may include a transparent or semi-transparent window 390 disposed at or near distal end 312.

Once the guide catheter is inserted into the small intestine (step 204), and placed so tools may reach the target location (e.g., the pancreatico-biliary system may be accessed), a balloon or equivalent device may be expanded (e.g., expandable portion 110 of FIG. 1 and/or expandable portion 310 of FIGS. 3A and 3B). For example, the expanding apparatus 102 of FIG. 1 may be used to introduce fluid into sheath 106 of FIG. 1 and expand the expandable portion 110 of FIG. 1 or 310 of FIG. 3 to a desired diameter. In some examples, the expanding portion 310 may be placed in a position so that tools within guide catheter 308 may reach the papilla 334. The expandable portion 310 may be expanded to a diameter based on the location of the expandable portion 310. For example, if the expandable portion 310 is located in the small intestine 302, expandable portion 310 may be expanded so as to contact the walls of the small intestine with sufficient pressure to anchor the expandable portion 310 (and thus the guide catheter 306) in the desired location. In some examples, the expandable portion may be expanded prior to rotating the guide catheter 308 into the desired position.

Once anchored (step 206), method 200 may proceed to step 208. An access device (e.g., a needle/knife and/or a tome) and/or an imaging device (a camera and/or Spy-Scope™) may already be disposed within the catheter prior to method 200 or may slide into the catheter after step 202, 204 and/or 206. Having the imaging device in place in advance of the anchoring step may allow the imaging device to be used to help position the guide catheter 308 at the desired position and/or orientation prior to it being anchored in place. An access device and/or an imaging device may exit the catheter through a distal opening and enter into the target area in the patient. FIG. 3A illustrates an exemplary system wherein no portion of the access device and the imaging device is disposed within the patient. FIG. 3B illustrates an exemplary system wherein the needle knife 352 is slidably disposed within a working channel of an imaging device 350 exit guide catheter 308 through a side opening proximal to the distal end 312 and a portion of both is disposed within the patient.

Figure 5B:
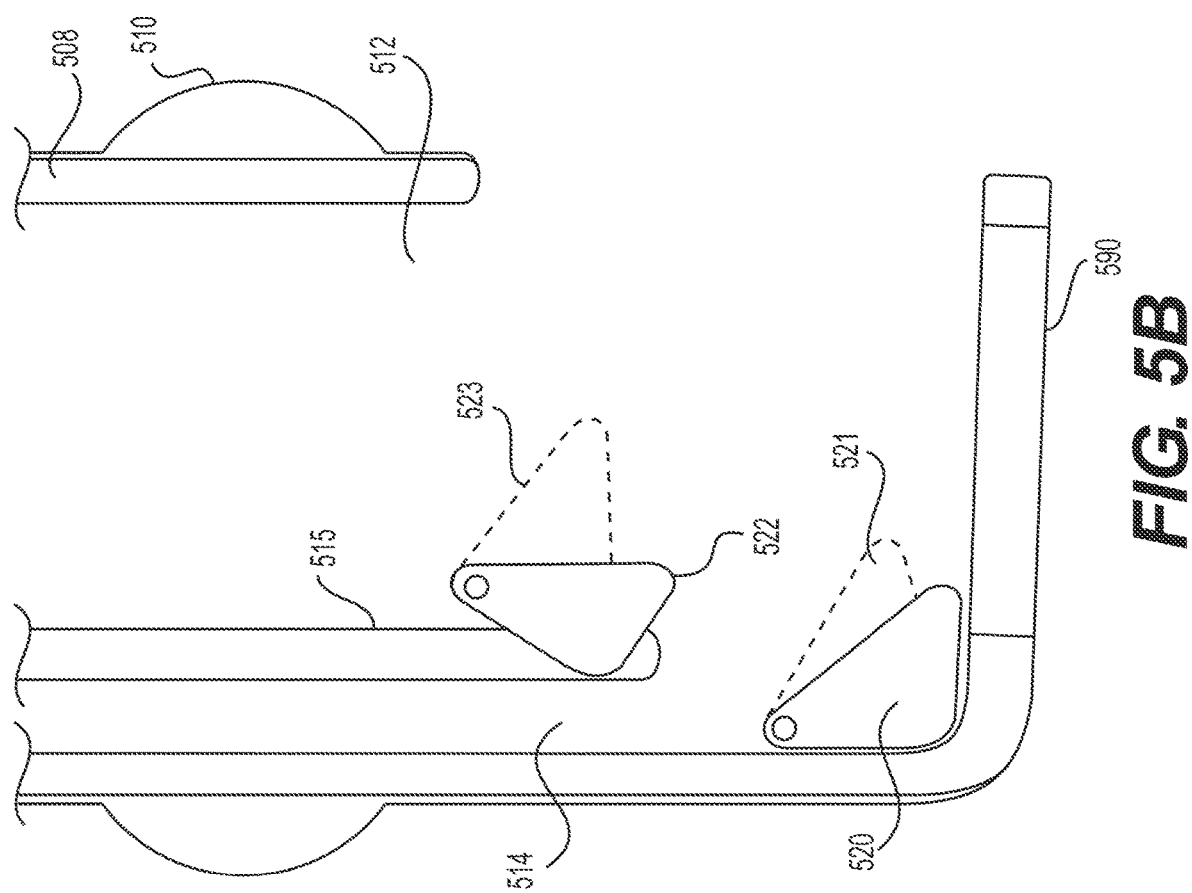
FIG. 5B illustrates an exemplary alternative embodiment of a distal portion of the guide catheter.

Step 208 may include adjusting at least one elevator so that any tools slidably disposed within the guide catheter may access the target location, e.g., the papilla or through the papilla. In some examples, an imaging device 350 and/or an access device 352 of FIG. 3B may be slidably disposed within the guide catheter 108 of FIG. 1 and/or guide catheter 308 of FIGS. 3A and/or 3B. The distal ends of imaging device 350 (including camera 348) and access device 352 (e.g., needle-knife and/or tome) may slide through a distal opening in the guide catheter 308. Elevator 320 may position these tools so they may access the papilla 334. In some embodiments, as shown in FIG. 3B, the access device 352 and the imaging device 350 are disposed within the same lumen of guide catheter 308 and/or positioned by a single elevator 320. FIGS. 4A and 4B provide greater detail on exemplary embodiments wherein the tools are slidably disposed within a single lumen and positioned by a single elevator. For example, a needle-knife may be slidably disposed within a working channel of an imaging device, and the imaging device may be slidably disposed within the single lumen. In some embodiments, the tools (e.g., access device 352 and/or imaging device 350) are disposed in separate lumens and/or positioned by separate elevators. For example, a tome may be slidably disposed within a first lumen, and an imaging device may be slidably disposed within a second lumen. Exemplary embodiments wherein the tools are disposed in separate lumens and positioned by separate elevators are illustrated in FIGS. 5A and 5B.

FIG. 4A illustrates a cross-sectional view of catheter 408. This view, for example, may be at any location distal of lumen 104 and proximal of a distal opening of guide catheter 108 of FIG. 1. As shown, the catheter 408 may be surrounded by expandable portion 410 and include lumen 412. Lumen 412 may have any cross-sectional shape and size. For example, lumen 412 may have a diameter between approximately 3.5 and approximately 9.5 mm, between approximately 4 and approximately 5 mm or approximately 4.2 mm. Lumen 412 may be configured to receive a medical device, tool, and/or instrument, e.g., an access device and/or imaging device.

FIG. 4B depicts an alternative configuration of a distal portion of guide catheter 408, including expandable portion 410, lumen 412, and an elevator represented in two alternative positions, elevator position 420 (depicted by the dotted line in the figure) and elevator position 421. Lumen 412 may be configured to receive tools, e.g., an access device and/or imaging device. Elevator position 421 may direct any tools extending through lumen 412 at a more distal angle than elevator position 420 would direct such tools. Lumen 412 and the associated elevator may receive and angle multiple tools. For example, as shown in FIG. 3B, both an access device and an imaging device may be positioned/directed by the same elevator (e.g., a needle-knife may be disposed within a working channel of the imaging device). In such embodiments, both devices may exit the guide catheter 408 at the same angle. In some examples, the elevator within lumen 412 may be fixed or locked in a desired position by, for example, locking mechanisms 155 and/or 156. Guide catheter 408 may include a transparent or semi-transparent window, e.g., window 490 at or near the distal end. An imaging device may be positioned (for example, when the elevator is in elevator position 421), so as to capture images through window 490. Such imaging may be used while inserting and/or positioning guide catheter 408.

Figure 5A:
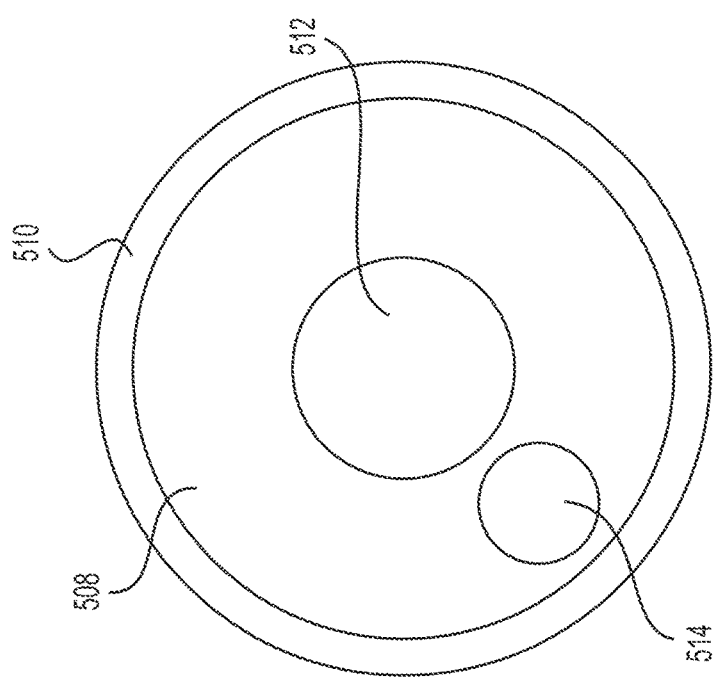
FIG. 5A illustrates an exemplary alternative embodiment of a cross-section of the guide catheter.

FIG. 5A illustrates a cross-sectional view of catheter 508. This view may, for example, be at any location distal of lumen 104 and proximal of the distal opening of guide catheter 108 of FIG. 1. As shown, the catheter 508 may be surrounded by expandable portion 510 and include lumens 512 and 514. Lumens 512 and 514 may have any cross-sectional shape and size. For example, lumens 512 and 514 may have a diameter between approximately 3.5 mm and approximately 5 mm, between approximately 4 mm and approximately 4.5 mm, or approximately 4.2 mm. In some embodiments, lumens 512 and 514 may have different cross-sectional shapes and/or sizes. For example, in FIG. 5A, lumen 514 has a diameter smaller than lumen 512. Lumens 512 and 514 may be separated be an interior wall 515 of guide catheter 508.

Guide catheter 518 may be devoid of visualization/imaging apparatus and/or tools. Lumens 512 and 514 may be configured to receive a medical device, tool, and/or instrument, e.g., an access device and/or imaging device. In some embodiments, the access device and the imaging device may be slidably disposed within one of lumens 512 or 514. In other embodiments, an access device may be disposed within one lumen and an imaging device in the other. For example, an access device (e.g., needle-knife or tome) may be slidably disposed within lumen 514 and an imaging device may be slidably disposed within lumen 512.

FIG. 5B depicts an alternative configuration of a distal portion of guide catheter 508, including expandable portion 510, lumen 512 including a first elevator represented in two alternative positions, elevator position 522 and elevator position 523 (depicted by the dotted line in the figure), and lumen 514 including a second elevator represented in two alternative positions, elevator position 520 and elevator position 521 (depicted by the dotted line in the figure). The first elevator may be attached and/or connected to the interior wall of guide catheter 508. The first elevator (e.g., the elevator included in lumen 512) may be proximal to the second elevator (e.g., the elevator included in lumen 514). In some examples, the imaging device may be proximal to the access device so that the operator can see where the access device is being delivered (and/or watch as the access device emerges from the guide catheter). Complete visualization of the access tool as it emerges from the guide catheter may prevent unintentional puncture and/or trauma to the tissue of the patient.

Elevator positions 520/522 may direct any tools extending through lumens 512 and 514, respectively, at a more distal angle than elevator positions 521/523 would direct such tools. Lumens 512 and 514 and the associated elevators may receive and position multiple tools. For example, lumen 512 may receive an access device, e.g., access device 352 of FIG. 3B and an imaging device, e.g., imaging device 350 of FIG. 3B. In other embodiments, lumens 512 and 514 an associated elevators may receive and position a single tool. For example, lumen 512 may receive an access device, e.g., access device 352 of FIG. 3B and lumen 514 may receive an imaging device, e.g., imaging device 350 of FIG. 3B. The elevator within lumen 512 and the elevator within lumen 514 may move independently of each other. In such examples, a tool disposed within lumen 512 be angled relative to the longitudinal axis of guide catheter 508 at a different angle than a tool disposed within lumen 514. Individual control of the elevators may allow for more flexibility for the operator to deliver the devices to desired locations. In other examples, the first and second elevators may be rotated in unison. In such embodiments, both devices may exit the guide catheter 508 at the same angle.

In some examples, lumen 512 may be centered, as shown in FIG. 5A. In other examples, lumen 512 may be offset from the central axis of guide catheter 508, as shown in FIG. 5B. Guide catheter 508 may include a transparent or semi-transparent window, e.g., window 590 at or near the distal end. An imaging device may be positioned (for example, when the elevator within lumen 512 is in elevator position 522), so as to capture images through window 590. Such imaging may be used while inserting and/or positioning guide catheter 508.

In some examples, the elevators within lumens 512 and/or 514 may be fixed or locked in a desired position. In some examples, the elevator within lumen 512 may be locked at a different angle than the elevator within lumen 514. The elevators may be locked by locking mechanisms 155 and/or 156 of FIG. 1.

Any of lumens 412, 512, and 514 may include any suitable coating. For example, a lumen may include a layer of lubricous material to facilitate insertion of any instrument and/or device. In some embodiments, lumens 412, 512, and/or 514 may be coated with a lubricous material to facilitate insertion of access device 352 of FIG. 3B and/or imaging device 350 of FIG. 3B.

The elevators disposed within lumens 412, 512, and/or 514 may include grooves (e.g., V or U-shaped grooves) to guide any tools disposed within the lumens. In some examples, the elevator may be configured to transition, at least partially out of the guide catheter, e.g., as shown in FIG. 3B. In other examples, the elevators, no matter the rotational position, are configured to remain within the guide catheter, e.g., as depicted in FIGS. 4B and 5B.

The elevators may be repositioned and/or rotated in any way, e.g., any way known in the art. For example, one end of the elevator may be attached to the interior wall of its associated lumen and/or pivot around a pin, screw, turning support, etc.

A distal end of a pull wire may be connected to the elevator. A proximal end of the pull wire may extend to an operator, e.g., through handle portion 118 and/or elevator control mechanisms 114 and 116 of FIG. 1. For example, elevator control mechanism 114 may be associated with the elevator disposed in lumen 512 of FIG. 5 and elevator control mechanism 116 may be associated with the elevator disposed in lumen 514 of FIG. 5. By means of a pull wire, the operator may control the placement of the tools (e.g., accessing device 352 and/or imaging device 350). For example, an elevator may be rotated counterclockwise about a pivot point by means of proximally pulling a pull wire connected to an upper portion of the elevator. Upon actuation of the pull wire through proximal movement thereof, the elevator may direct any tool disposed within the associated lumen in a more proximal direction by altering the angle at which the tool exits the guide catheter (e.g., guide catheter 308 of FIG. 3B). FIG. 3B illustrates an exemplary embodiment of the resulting position of elevator 320, accessing device 352, and/or imaging device 350. In some examples, a threaded rod may be connected to each elevator.

Once the accessing device and/or the imaging device are appropriately positioned (step 208), method 200 may proceed to step 210 and the pancreatico-biliary system may be accessed, at least in part, by using the access device (e.g., access device 352 of FIG. 3B). For example, access device 352 and/or imaging device 350 may be advanced through the papilla of Vater 334 of FIG. 3B to the intended target. In some examples, the intended target may be, for example, the pancreatic duct 336 or the common bile duct 338. The operator may advance access device 352 and/or imaging device 350 through the papilla 334 and then advance the access 352 device and/or imaging device 350 into the intended target duct.

Once desired procedure is complete, any tool (e.g., access device 352 and/or imaging device 350) that may have exited guide catheter 308 may be retracted back into guide catheter 308. In embodiments, like that illustrated in FIG. 3B, wherein the elevator(s) is configured to transition to a position external to the guide catheter 308, the externally positioned elevator(s) may similarly be retracted/repositioned into the guide catheter 308. Expanding portion 110 of FIG. 1 and expanding portion 310 of FIG. 3 may be deflated. In some embodiments, a syringe may be used to pull the fluid back out of expanding portion 110 through sheath 104. In some embodiments, a vacuum source may be activated to suction the fluid out of expanding portion 110. In some embodiments, a seal (e.g., external to the patient's body) may be removed and/or broken allowing the expanding fluid to exit the expanding portion 110.

Once any tools that had exited the guide catheter are retracted into the guide catheter and the anchoring mechanism (e.g., expanding portion 110) is deactivated, guide catheter 308 may be removed from the body (e.g., pulled back through small intestine 302, stomach 318, esophagus 304, and out through the mouth or nose).

The many features and advantages of the disclosure are apparent from the detailed specification, and thus, it is intended by the appended claims to cover all such features and advantages of the disclosure which fall within the true spirit and scope of the disclosure. Further, since numerous modifications and variations will readily occur to those skilled in the art, it is not desired to limit the disclosure to the exact construction and operation illustrated and described, and accordingly, all suitable modifications and equivalents may be resorted to, falling within the scope of the disclosure.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:
    a guide catheter, including a first lumen and a second lumen;
    a first elevator disposed in the first lumen, wherein the first elevator is coupled to the guide catheter via a first pivot axis, and wherein the first elevator is rotatable about the first pivot axis relative to the first lumen for elevating a first tool insertable into the first lumen; and
    a second elevator disposed in the second lumen, wherein the second elevator is coupled to the guide catheter via a second pivot axis, and wherein the second elevator is rotatable about the second pivot axis relative to the second lumen for elevating a second tool insertable into the second lumen;
    wherein the first pivot axis is parallel to the second pivot axis, wherein the first lumen has a first diameter and the second lumen has a second diameter smaller than the first diameter, and wherein a central longitudinal axis of the first lumen is coaxial with a central longitudinal axis of the guide catheter.

2. The medical device of claim 1, wherein the first elevator is rotatable independent of the second elevator.

3. The medical device of claim 2, wherein the first elevator is rotatable in unison with the second elevator.

4. The medical device of claim 1, further comprising the first tool and the second tool, wherein the first tool is an imaging device, and wherein the second tool is an access device.

5. The medical device of claim 1, further comprising an expandable portion disposed on the outside of the guide catheter.

6. The medical device of claim 5, further comprising an expanding apparatus, configured to expand the expandable portion.

7. The medical device of claim 1, further comprising a first elevator control mechanism at a proximal end of the medical device configured to rotate the first elevator, and a second elevator control mechanism at the proximal end of the medical device configured to rotate the second elevator.

8. The medical device of claim 1, wherein the first pivot axis is proximal of the second pivot axis.

9. The medical device of claim 8, wherein an entirety of the first elevator is proximal of the second elevator.

10. The medical device of claim 1, wherein the first pivot axis is radially inward of the second pivot axis.

11. A guide catheter assembly, comprising:
    a shaft;
    a first lumen extending through the shaft;
    a first elevator in the first lumen, wherein the first elevator is coupled to the shaft via a first pivot axis, and wherein the first elevator is rotatable about the first pivot axis relative to the first lumen;
    a second lumen extending through the shaft; and
    a second elevator in the second lumen, wherein the second elevator is coupled to the shaft via a second pivot axis, and wherein the second elevator is rotatable about the second pivot axis relative to the second lumen;
    wherein the first pivot axis is proximal of the second pivot axis, wherein a central axis of the first lumen is coaxial with a central axis of the shaft, and wherein the first lumen has a first diameter, and the second lumen has a second diameter smaller than the first diameter.

12. The guide catheter assembly of claim 11, wherein the first elevator is rotatable independently of the second elevator.

13. The guide catheter assembly of claim 11, wherein the first elevator and the second elevator are rotatable in unison.

14. The guide catheter assembly of claim 11, further comprising:
    an expandable portion disposed around at least a portion of the shaft of the guide catheter assembly;
    an exterior; and
    a sheath at least partially sealed to the exterior and fluidly connected to the expandable portion.

15. The guide catheter assembly of claim 11, further comprising a first tool insertable within the first lumen, and a second tool insertable within the second lumen, wherein the first tool is an imaging device, and wherein the second tool is at least one of a needle-knife or a tome.

16. A medical device, comprising:
    a guide catheter, including a first lumen and a second lumen, wherein the first lumen has a first diameter, and the second lumen has a second diameter smaller than the first diameter, and wherein a central axis of the first lumen is coaxial with a central axis of the guide catheter;
    a first elevator disposed in the first lumen, wherein the first elevator is coupled to the guide catheter via a first pivot axis, and wherein the first elevator is rotatable about the first pivot axis relative to the first lumen for elevating a first tool insertable into the first lumen; and
    a second elevator disposed in the second lumen, wherein the second elevator is coupled to the guide catheter via a second pivot axis, and wherein the second elevator is rotatable about the second pivot axis relative to the second lumen for elevating a second tool insertable into the second lumen;
    wherein the first pivot axis is parallel to the second pivot axis, and wherein the first pivot axis is proximal of the second pivot axis.

17. The medical device of claim 16, wherein the first pivot axis is radially inward of the second pivot axis.

* * * * *